(12) United States Patent
Alhazmi

(10) Patent No.: US 10,207,981 B2
(45) Date of Patent: Feb. 19, 2019

(54) PRODUCTION OF TEA 85% DIRECTLY WITHOUT BLENDING WITH PURE CUT OF DEA 99%

(71) Applicant: SABIC GLOBAL TECHNOLOGIES B.V., Bergen of Zoom (NL)

(72) Inventor: Naeem Alhazmi, Riyadh (SA)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 15/313,659

(22) PCT Filed: May 27, 2015

(86) PCT No.: PCT/IB2015/053976
§ 371 (c)(1),
(2) Date: Nov. 23, 2016

(87) PCT Pub. No.: WO2015/181748
PCT Pub. Date: Dec. 3, 2015

(65) Prior Publication Data
US 2017/0096387 A1    Apr. 6, 2017

Related U.S. Application Data

(60) Provisional application No. 62/003,312, filed on May 27, 2014.

(51) Int. Cl.
C07C 213/04    (2006.01)
C07C 213/10    (2006.01)

(52) U.S. Cl.
CPC .......... *C07C 213/04* (2013.01); *C07C 213/10* (2013.01); *Y02P 20/127* (2015.11)

(58) Field of Classification Search
None
See application file for complete search history.

(56) References Cited

U.S. PATENT DOCUMENTS 2,523,236 A    2/1958    Lowe et al.
3,453,183 A    7/1969    Okubo et al.
(Continued)

FOREIGN PATENT DOCUMENTS

CA    2542546 A1    6/2005
CN    103772211 A    5/2014
(Continued)

OTHER PUBLICATIONS

Merluzzi et al. AIChE Journal 18, No. 4, 1972, 739-744.*
(Continued)

*Primary Examiner* — Clinton A Brooks
(74) *Attorney, Agent, or Firm* — Cantor Colburn LLP

(57) ABSTRACT

Systems and methods for producing a triethanolamine product stream with a degree of purity of 85% by weight from the triethanolamine distillation columns in a reactive distillation process without blending the TEA 99 product stream with a pure cut of DEA 99%. The desired triethanolamine product stream can include 85% TEA and 15% DEA and can be created by using a dummy stream at the triethanolamine column via (1) increasing the bottom stream flow rate of the diethanolamine column, and/or (2) reducing the TEA 99 product stream at the triethanolamine column. The bottom stream flow rate at the diethanolamine column can be increased by 80 kilograms per hour and the triethanolamine product stream flow rate can be reduced by 500 kilograms per hour. This process can result in up to a 23 degree temperature reduction in the triethanolamine column, which can improve the color properties of the triethanolamine product.

17 Claims, 2 Drawing Sheets

(56) References Cited

U.S. PATENT DOCUMENTS

| | | |
|---|---|---|
| 3,849,262 A | 11/1974 | Cocuzza |
| 4,169,856 A | 10/1979 | Cocuzza et al. |
| 4,355,181 A | 10/1982 | Willis, Jr. et al. |
| 5,545,757 A | 8/1996 | Hammer et al. |
| 6,323,371 B2 | 11/2001 | Ruider et al. |
| 6,696,610 B2 | 2/2004 | Preschel et al. |
| 6,846,959 B2 | 1/2005 | Garg et al. |
| 7,164,044 B2 | 1/2007 | Morishita et al. |
| 7,550,632 B2 | 6/2009 | Haese et al. |
| 7,560,594 B2 | 7/2009 | Haese et al. |
| 8,466,323 B2 | 6/2013 | Melder et al. |
| 2002/0123653 A1 | 9/2002 | Tsuneki et al. |
| 2006/0293541 A1 | 12/2006 | Reif et al. |
| 2014/0061020 A1 | 3/2014 | Schmidt et al. |

FOREIGN PATENT DOCUMENTS

| | | |
|---|---|---|
| EP | 0690043 A2 | 1/1996 |
| EP | 2177501 A1 | 4/2010 |
| GB | 1092449 A | 11/1967 |
| IN | 238069 | 7/2007 |
| JP | 2004238290 A | 8/2004 |
| WO | 0153250 A1 | 7/2001 |
| WO | 2004113268 A1 | 12/2004 |
| WO | 2015151057 A1 | 10/2015 |
| WO | 2015155667 A1 | 10/2015 |
| WO | 2015181751 A1 | 12/2015 |

OTHER PUBLICATIONS

International Search Report for International Application No. PCT/IB2015/053976; dated Sep. 3, 2015; 4 Pages.

Japanese Patent No. 2004238290; Date of Publication: Aug. 26, 2004; Abstract Only, 2 pages.

Tsuneki, H., "Development of Diethanolamine Selective Production Process Using Shape-Selective Zeolite Catalyst"; Catalysis Surveys Asia, 2010, vol. 14, pp. 116-123.

Written Opnion of the International Search Report for International Application No. PCT/IB2015/053976; dated Sep. 3, 2015; 6 Pages.

Chinese Patent No. 103772211; Date of Publication: May 7, 2014; Abstract Only, 2 pages.

* cited by examiner

PRODUCTION OF TEA 85% DIRECTLY WITHOUT BLENDING WITH PURE CUT OF DEA 99%

CROSS REFERENCE TO RELATED APPLICATIONS

This application is a 371 of International Application No. PCT/IB2015/053976, filed May 27, 2015, which claims priority to U.S. Application No. 62/003,312, filed May 27, 2014 both of which are incorporated herein by reference in their entirety.

TECHNICAL FIELD

The present application relates to a process for the production of ethanolamines, specifically, to a process for producing triethanolamine with a degree of purity equal to or greater than 85% by weight without blending with pure cut diethanolamine with a degree of purity equal to or greater than 99% by weight.

BACKGROUND

Ethanolamines, individually and in combination have many uses in the chemical industries. For example, ethanolamines can be used as corrosion inhibitors, lubricants and scouring agents for gas sweetening, detergents and specialty cleaners, concrete admixtures, flexible urethane foam catalysts, personal care products, photographic emulsions, solvents, dye intermediates, rubber accelerator, emulsifiers, ink additives, oil additives, alkalization of water in steam cycles of power plants and nuclear plants with pressurized water reactors, pesticides and pharmaceutical intermediates, natural gas is also used as acid gas absorption solvent. Ethanolamines can also be used in the semiconductor field for wafer cleaning and photoresist striping applications because of their surfactant properties. Global demand for ethanolamines is increasing, and is projected to exceed 1.605 million tons by 2015.

Ethanolamines are flammable, corrosive, colorless, viscous liquids that are produced by the reaction of ammonia ($NH_3$) and halohydrins or ethylene oxide ($C_2H_4O$) (EO). EO, however, is more widely used for commercial processes. To produce ethanolamines commercially, aqueous ammonia and ethylene oxide are contacted in a single stage or multi stage reaction chamber at a temperature of 50° C. to 257° C. There are three types of ethanolamines: MEA ($H_2NCH_2CH_2OH$); Diethanolamine ($HN(CH_2CH_2OH)_2$), also referred to as DEA; and Triethanolamine ($N(CH_2CH_2OH)_3$), also referred to as TEA. The formation of MEA, DEA or TEA depends on whether an ammonia molecule reacts with 1, 2 or 3 EO molecules. The reactions have a parallel consecutive mechanism, so that the three products (MEA, DEA and TEA) are obtained simultaneously. Water is used as a catalyst in ethanolamine reactions.

Due to the demand for ethanolamines in the petrochemical industry, needs exist for producing higher-yield ethanolamine product streams via a cost-effective process.

SUMMARY

Disclosed herein, in various embodiments, are systems and methods for producing triethanolamine in a non-reactive distillation column.

A method for producing triethanolamine from a non-reactive distillation column, comprises: mixing an ammonia solution comprising 30% to 40% by weight ammonia with ethylene oxide in a reactor to create a resultant product stream, wherein said resultant product stream comprises ethanolamines, unreacted ammonia and water; removing 30% to 50% by weight of the unreacted ammonia and from the resultant product stream to create a stripped product stream; transferring the stripped product stream to a stage of a diethanolamine distillation column to create a resultant product stream, wherein said resultant product stream comprises triethanolamine with a degree of purity equal to or greater than 85% by weight and 10% to 15% by weight of diethanolamine; adjusting bottom stream flow rate at the diethanolamine distillation column from 1% to 4% above a base value bottom stream flow rate; transferring the resultant product stream to at least one stage of a triethanolamine distillation column to create a triethanolamine product stream, wherein the triethanolamine product stream comprises triethanolamine with a degree of purity greater than or equal to 99% by weight and 0.1% to 0.6% by weight of diethanolamine; adjusting flow rate for the triethanolamine product stream by 10% to 20% below a base value flow rate; and removing a portion of the resultant product stream via a dummy stream to create a triethanolamine resultant stream, wherein said triethanolamine resultant stream comprises triethanolamine with a degree of purity greater than or equal to 85% by weight and 10% to 15% by weight of diethanolamine.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION OF THE INVENTION

Embodiments disclosed herein can provide an improved process for producing TEA with a degree of purity equal to or greater than 80% by weight, and preferably with a degree of purity equal to or greater than 85% by weight, known, conventionally as "TEA 85", from vacuum distillation columns in a non-reactive distillation apparatus. This method can be practiced over a wide range of processing conditions including but not limited to the concentrations of reactants, flow rates of reactants, temperatures, and pressures. The process can be conducted in the presence or absence of a catalyst, wherein the catalyst is preferably water. The process can be conducted in aqueous or non-aqueous phase. A desired output product in the process can be manipulated to include various ratios of MEA, DEA, and TEA by selecting appropriate processing conditions. The process as described herein are exemplary processes only and used for illustrative purposes. Other variations and combinations of steps and components can be used as necessary.

Figure 1:
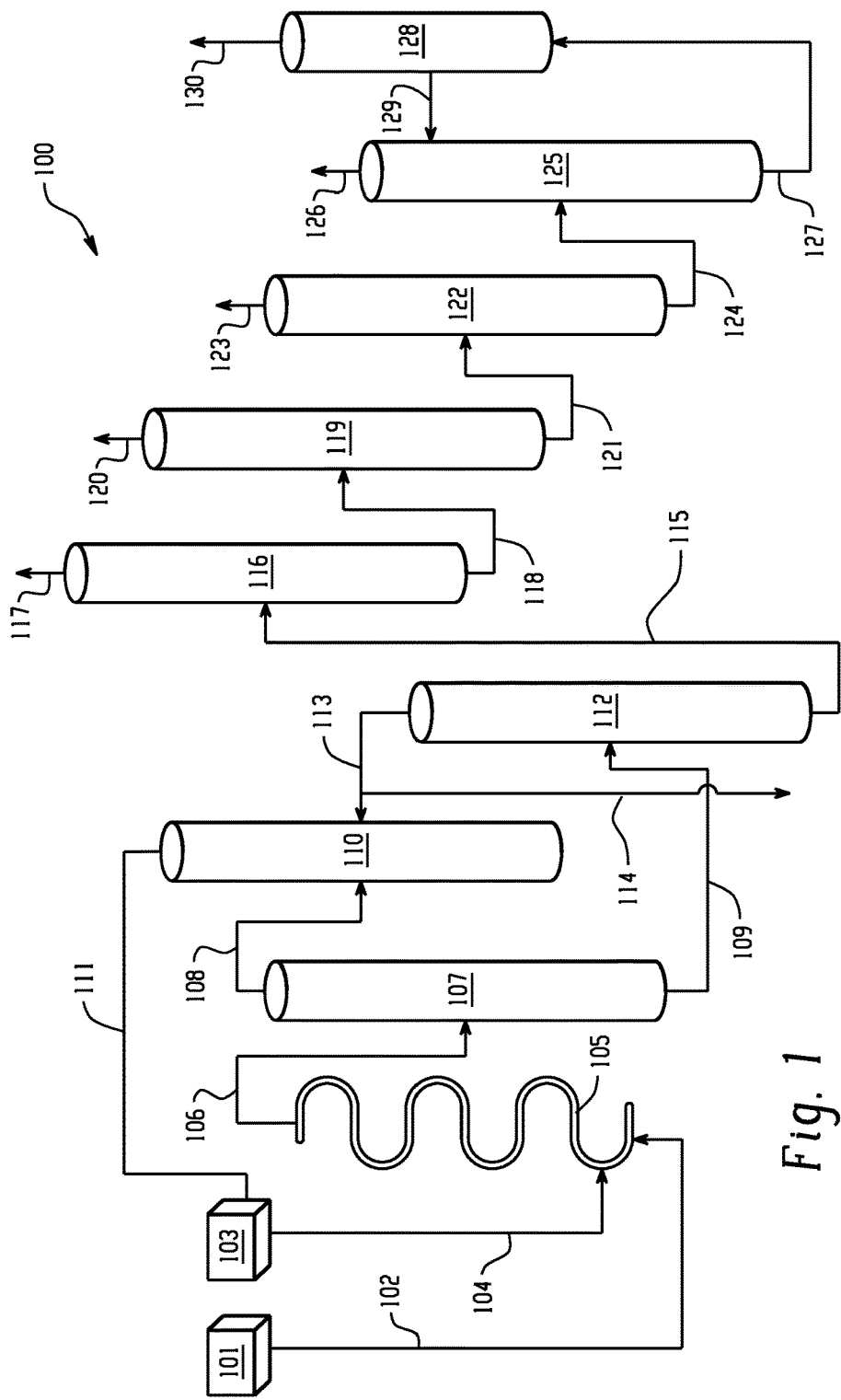
FIG. 1 is a schematic representation of an ethanolamine production process according to one embodiment.

Referring to FIG. 1, there is shown a schematic representation of an ethanolamine production process according to one embodiment. The process 100 can include a reactor 105, in which EO can be reacted with excess ammonia and water in an aqueous solution to form an ethanolamine reaction product including MEA, DEA and TEA; an ammonia stripper 107 for stripping the unreacted ammonia from the reaction product and for removing the excess ammonia and some water by distillation; a vacuum drying column 112 for evaporating water from the stripped reaction product to create a dehydrated reaction product; and an amine distillation component for separating the dehydrated reaction product into MEA, DEA and TEA. In some alternatives, the process 100 can also include an ammonia absorber 110 and ammonia solution storage 103 for recycling the excess ammonia stripped from the reaction product where ammonia solution storage 103 can be fed to ammonia absorber through line 111. Ammonia absorber 110 and ammonia solution storage 103 can be fed to the reactor 105. In some alternatives, the process 100 can also include EO storage 101. In some alternatives, the ammonia striper 107, the drying column 112, and the distillation or splitter columns can be carried out with one or more plate-type columns. In some alternatives, the one or more plate-type columns can include a reaction zone (top section) and a stripping zone (bottom section). In some alternatives, the columns can include multiple plates or stages, for example, 5-20 stages. The reactor 105 used in the process 100 can be an isothermal reactor, an adiabatic reactor or other known reactor. A tubular reactor externally cooled by circulating water can be used. In some alternatives, the length of the reactor 105 can be approximately 2 meters to approximately 35 meters, for example, 2 meters to 35 meters. In some alternatives, the diameter of the reactor 105 can be approximately 0.2 meters to approximately 0.5 meters, for example, 0.2 meters to 0.5 meters.

The following example are merely illustrative of the systems and methods disclosed herein and are not intended to limit the scope hereof. Unless otherwise stated, the examples disclosed herein were based upon simulations.

EXAMPLE 1

100% of Base Case at TEA Column 125

Figure 2:
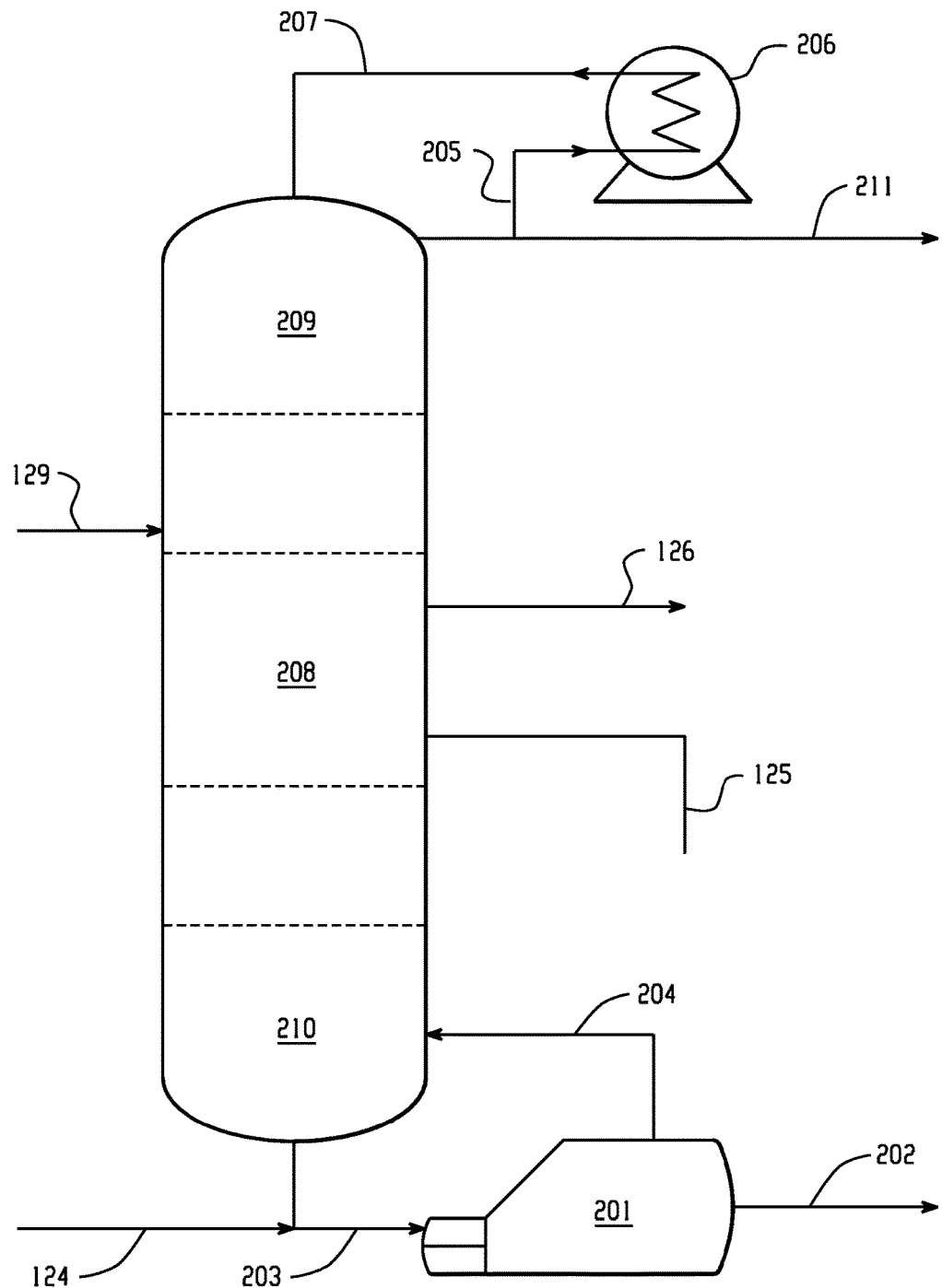
FIG. 2 an ASPEN™ simulation of a triethanolamine column according to one embodiment.

Referring to FIG. 2, there is shown an ASPEN™ simulation of a TEA column for the production of TEA 85 and TEA with a degree of purity equal to or greater than 99.2% by weight, for example, with a degree of purity equal to or greater than 99.4% by weight, for example, with a degree of purity equal to or greater than 99.7% by weight, and for example, with a degree of purity equal to or greater than 99.9% by weight, conventionally known as "TEA 99", according to one embodiment. A simulation model can be developed to evaluate the process 100 and component of the process 100. The model can be validated against actual plant behavior. Data from actual plant behavior can be input into the model and can be used to tweak the model. The model can be developed using Aspen™ simulation software (Aspen Plus™ and Aspen Custom Modeler™) or other simulation software, such as Simulation Sciences (SimSci) Pro/II™. The model can use processing conditions data from a plant in Saudi Arabia, capable of producing approximately 90,000—approximately 110,000 tons of ethanolamine per year. The plant is also capable of producing approximately 700,000 tons of Mono-ethylene glycol (MEG) per year. In some alternatives, the model can be developed with Oxiteno process flow diagram (PFD) data for the ethanolamine production process. These simulations can be labeled as the base case.

In some alternatives, the process 100 can utilize six stages of tubular reactors 105 connected in series with intercoolers between the reactors 105. In some alternatives, the intercoolers can consist of a bundle of U-tubes, maintained at temperatures of approximately 37° C. to approximately 70° C. For example, the temperatures of the U-tubes can be maintained at temperatures of 41° C.-43° C. to 60° C.-63° C. The temperature at the tubular reactors 105 can be cooled down from 60° C.-63° C. at the outlet of each stage of the tubular reactors 105 to 41° C.-43° C., where it can be fed to the inlet of each stage of the tubular reactors 105 by means of an intercooler using a circulating or evaporating coolant as the cooling media. In some alternatives, the coolant can be water.

An aqueous ammonia feed from ammonia storage 103 can be introduced to, for example, the first stage of the reactor 105 via line 104. An alkylene oxide, such as, for example, EO from EO storage 101 can also be introduced to the first stage of the reactor 105 via line 102. In some alternatives, the ammonia feed from ammonia storage 103 and the EO feed from EO storage 101 can be combined before being introduced to the first stage of the reactor 105. In some alternatives, the aqueous ammonia solution can include 30-40% by weight of ammonia and 50-70% by weight of water. For example, the ammonia solution can include approximately 33-35% by weight of ammonia, for example, 33-35% by weight of ammonia and approximately 62% by weight of water, for example, 62% by weight of water. In some alternatives, the % by weight of ammonia can be maintained below 50% to increase the production of MEG. In some alternatives, the ethanolamines produced by the process 100 can be recycled back into reactor 105 in order to adjust the desired MEA:DEA:TEA ratio. In some alternatives, approximately 1-5% by weight of MEA can be added to the aqueous ammonia solution, for example, 1-5% by weight of MEA. In some alternatives, approximately 1-5% by weight of DEA can be added to the aqueous ammonia solution, for example, 1-5% by weight of DEA. For example, approximately 2.7% by weight MEA and approximately 2.2% by weight DEA can also be added to the aqueous ammonia solution, for example, 2.7% by weight MEA and 2.2% by weight DEA. In some alternatives, the ammonia in the aqueous ammonia solution can be freshly added ammonia, recycled ammonia, or a combination comprising at least one of the foregoing. In some alternatives, the fresh ammonia can be fed directly into a reactor 105 or at some other point in the process 100 (e.g., to the ammonia stripper 107). In some alternatives, ammonia suitable for the reaction can be anhydrous or a solution of ammonia and water.

In some alternatives, the required EO for the reaction can be split evenly across the stages of the reactor 105. The flow of EO to each stage of the reactor 105 via line 102 can be maintained at approximately 1500 kilograms per hour (kg/hr) to approximately 1800 kg/hr, for example, 1500 kg/hr to 1800 kg/hr. The flow of EO to each stage of the reactor 105 can be can be maintained at 1714.2 kg/hr to produce the desired EO conversion at the outlet of each stage of the reactor 105. In some alternatives, the EO flow rate to each stage of the reactor 105 can be one sixth of the total EO flow rate for line 102, for example, one-sixth of a total EO flow rate of 10,285 kg/hr. The flow rate of the EO can ensure that approximately eighty-six percent of the EO can be converted in the reactions occurring at the first four stages of the reactor 105. Approximately ninety-nine percent, for example, 99% of the EO can be converted in the reaction occurring at the fifth stage of the reactor 105 and greater than ninety-nine percent of the EO can be converted in the reaction occurring at the sixth stage of the reactor 105. In some alternatives, the EO flow rate to each stage of the reactor 105 can depend on the production rate of the ethanolamines. The pressure at each stage of the reactor 105 can be maintained at approximately 15 barg to approximately 30 barg, for example, 15 barg to 30 barg. For example, the pressure at each stage of the reactor 105 can be maintained between approximately 19 barg to approximately 24 barg to avoid the evaporation of EO and ammonia, for example, 19 barg to 24 barg. The reactions in the reactor 105 can form a reaction product effluent, which can include ethanolamines, unreacted/excess ammonia, any other unreacted components (e.g., water and the like), and optionally one or more reaction by-products, such as, for example, MEG.

The resultant product stream can be introduced via line 106 above the fourth stage of the ammonia stripper 107, which can include approximately sixteen stages. The feed rate for line 106 can be approximately 58,170 kg/hr to approximately 58,190 kg/hr, for example, 58,170 kg/hr to 58,190 kg/hr, for example, at a feed rate of 58,180 Kg/hr. The ammonia stripper 107 can remove the excess or unreacted ammonia from the reaction product effluent. The ammonia stripper 107 can operate at a pressure of approximately 1 barg to approximately 5 barg, for example, 1 barg to 5 barg, and for example, approximately 3.5 barg to approximately 3.6 barg, for example 3.5 barg to 3.6 barg. A flow including ethanolamines, byproducts and the remaining water can be extracted at the foot of the ammonia stripper 107 via line 109 and fed to drying column 112 where a dehydrated mixture of ethanolamines can be obtained by the evaporation of the remaining water. The temperature at the foot of the ammonia stripper 107 can be approximately 150° C. to approximately 165° C., for example, 150° C. to 165° C. and for example, approximately 158.2° C. to approximately 159.6° C., for example, 158.2° C. to 159.6° C. The flow can include approximately 35-50% by weight water, for example, 35-50% by weight water and more preferably, approximately 40-43% by weight of water, for example, 40-43% by weight of water. In some alternatives, part of the flow collected from the head of the ammonia stripper 107 via line 108, which can include approximately 90-99%, for example, 90-99%, by weight of water and negligible quantities of ethanolamine can be refluxed into the drying column 112 at a stage below the sixteenth stage via line 201. For example, the flow can include approximately 98.31% by weight of water and negligible quantities of ethanolamine, for example, 98.31% by weight of water.

In some alternatives, a second flow, which can include approximately 35-45% by weight ammonia and approximately 40-60% by weight of water, for example, 35-45% by weight ammonia and 40-60% by weight of water, negligible quantities of ethanolamines and MEG can be collected from the head of the ammonia stripper 107 via line 108 and conveyed to an ammonia absorber 110. For example, the flow can include approximately 40% by weight of unreacted ammonia, for example, 40% by weight of unreacted ammonia, approximately 59% by weight of water, for example, 50% by weight of water, negligible quantities of ethanolamines and MEG. The overhead vapors of the ammonia stripper 107 can be cooled and condensed and then fed to an ammonia absorption column 110 via line 108. Fresh ammonia makeup can be fed into the ammonia absorption column 110 and both streams can form part of the aqueous ammonia feed to the reactor 105 via line 104. The temperature at the top of the ammonia stripper 107 can be approximately 130° C. to approximately 140° C., for example, 130° C. to 140° C., and for example, approximately 133.6° C. to approximately 135.2° C., for example 133.6° C. to 135.2° C.

The stripped resultant product effluent from line 109 can be introduced to the drying column 112 above the second stage of the drying column at a feed rate of approximately 20,000 kg/hr to approximately 30,000 kg/hr, for example, 20,000 kg/hr to 30,000 kg/hr. For example, the feed rate can be approximately 24,611 kg/hr, for example, 24,611 kg/hr. The resultant product effluent from line 109 can be introduced at the ninth stage of the drying column 112. The drying column 112 can remove any water still present in the stripped resultant product effluent by evaporation of the remaining water. The water can leave the drying column 112 as a vapor via line 113. In some alternatives, the vapor can be added as a recycled water stream to the drying column 112 to ensure that no MEA, DEA or TEA leaves the drying column 112 together with the vapor. In some alternatives, water recovered from the drying column 112 via line 113 can be recycled for use in the ammonia absorber 110. In some alternatives, a portion of the water recovered from the drying column 112 via line 113 can also be recycled for use throughout the process 100 via line 114. The drying column 112 can be operated at a pressure of approximately 260 millibar (mbar) to approximately 280 mbar, for example, 260 mbar to 280 mbar, for example, approximately 270 mbar to approximately 273 mbar, for example, 270 mbar to 273 mbar. The drying column 112 can include a heat exchanger and a condenser.

The dehydrated resultant product stream from the drying column 112 including trace amounts of water, ethanolamines and byproducts can be fed to the MEA column 116 via line 115 at a point between the top and bottom of the MEA column 116 to create a DEA resultant product stream by removing substantially all of the MEA in the dehydrated resultant product stream. MEA product can leave MEA column 116 through line 117.

The resultant DEA product stream including trace amounts of MEA, DEA, TEA and byproducts from the MEA column 116 can be fed to the DEA columns 119 and/or 122 via lines 118 and/or 121, respectively, to create a TEA product stream including TEA 85, TEA 99 and approximately 10% by weight of DEA to approximately 15% by weight of DEA, for example, 10% by weight to 15% by weight of DEA, and for example, approximately, 15% by weight of DEA and byproducts, for example, 15% by weight of DEA and byproducts. DEA product can leave DEA column 119 through line 120 and DEA product can leave DEA column 122 through line 123.

The TEA product stream can be fed to, for example, the eighth stage of the TEA column 125 via line 124. The flow rate for the product stream can be approximately 4000 kg/hr to approximately 4300 kg/hr, for example, 4000 kg/hr to 4300 kg/hr, for example, approximately 4130 kg/hr, for example, 4130 kg/hr. The TEA column 125 can include, for example, eight stages. TEA heavy ends 202 from the bottom of the TEA column 125 can be fed in to, for example, the seventh stage of the TEA column 125 via line 129. In some alternatives, TEA heavy ends 202 can be sent to an evaporator 128 via line 127. Other product can leave evaporator 128 via line 130. The evaporator 128 can then recycle the TEA heavy ends 202 back to the TEA column 125 via line 129. In some alternatives, the flow rate of the TEA heavy ends 202 can be approximately 150 kg/hr to approximately 200 kg/hr, for example, 150 kg/hr to 200 kg/hr and for example, approximately 188.98 kg/hr, for example, 188.98 kg/hr. In some alternatives, the TEA heavy ends 202 can contain approximately 150 kg/hr to approximately 200 Kg/hr of TEA, for example, 150 kg/hr to 200 kg/hr, for example, approximately 188.96 kg/hr, for example, 188.96 kg/hr, and approximately 0.01kg/hr to approximately 0.05 kg/hr of DEA, for example, 0.01 kg/hr to 0.05 kg/hr, for example, approximately, 0.02 kg/hr of DEA, for example, 0.02 kg/hr of DEA. In some alternatives, the evaporator 128 can reduce the TEA content in the TEA heavy ends 202 and can possibly reduce the amount TEA heavy ends 202 produced. In some alternatives, the TEA feed from the bottom of the TEA column 125 to the evaporator 128 can be approximately 280 kg/hr to approximately 3450 Kg/hr, for example, 280 kg/hr to 3450 kg/hr, for example, approximately 310 kg/hr, for example, 310 kg/hr.

The TEA feed from the bottom of the TEA column 125 to the evaporator 128 can include approximately 0.5 kg/hr to approximately 5 kg/hr, for example, 0.5 kg/hr to 5 kg/hr, for example, approximately 1 kg/hr of DEA, for example, 1 kg/hr of DEA. The total TEA feed from the bottom of the TEA column 125 to the evaporator 128 can be approximately 285 kg/hr to approximately 330 kg/hr, for example, 285 kg/r to 330 kg/hr, for example, approximately 311 kg/hr, for example, 311 kg/hr. The TEA column 125 can be operated at a pressure of approximately 1 mbar to approximately 7 mbar, for example, 1 mbar to 7 mbar, for example, approximately 2.7 mbar to approximately 4.4 mbar, for example, 2.7 mbar to 4.4 mbar. The TEA column 125 can be operated at a temperature of approximately 150° C. to approximately 200° C., for example, 150° C. to 200° C., for example, approximately 171.2° C. to approximately 181.2° C., for example, 171.2° C. to 181.2° C. A condenser 206 with a duty of approximately 1000 kiloWatts (kW) to approximately 1600 kW, for example, 1000 kW to 1600 kW, for example, approximately 1441 kW, for example, 1441 kW, can keep the top stages of the TEA column 125 at a temperature of approximately 100° C. to approximately 200° C., for example, 100° C. to 200° C., for example, approximately 168° C. to approximately 175° C., for example, 168° C. to 175 ° C., and for example, at approximately 171.4° C., for example, 171.4 ° C. A reboiler 201, with a duty of approximately 1000 kW to approximately 1600 kW, for example, 1000 kW to 1600 kW, for example, approximately 1424 kW, for example, 1424 kW can keep the bottom stages of the TEA column 125 at a temperature of approximately 150° C. to approximately 200° C., for example, 150° C. to 200° C., for example, approximately 181.2° C., for example, 181.2° C. The TEA column 125 can be operated at a reflux rate of approximately 4000 kg/hr to approximately 5000 kg/hr, for example, 4000 kg/hr to 5000 kg/hr, for example, approximately 4400 kg/hr, for example, 4400 kg/hr. The TEA column 125 can be operated with a bottom rate of approximately 200 kg/hr to approximately 500 kg/hr, for example, 200 kg/hr to 500 kg/hr, for example, approximately 311 kg/hr, for example, 311 kg/hr.

A stream, which can include TEA 99, TEA heavy ends 202 and byproducts can be collected at the eighth stage 210 of the TEA column 125, and fed to a reboiler 201 via line 203. A stage 208 between the first stage 209 and the eighth stage 210 of the TEA column 125 is also shown in FIG. 2. For example, stage 208 can be the second, third, fourth, fifth, sixth, or seventh stage. The TEA heavy ends can include TEA and traces of DEA, TEA EO, and DEA EQ. TEA 99 can be distilled and returned to the TEA column 125 via line 204. The TEA heavy ends 202 rich stream can exit the heat exchange 201 via line 127 for further processing by the evaporator 128 and TEA column 125.

The flow rate of the TEA 99 collected from line 126 can be approximately 3500 kg/hr to approximately 4500 kg/hr, for example, 3500 kg/hr to 4500 kg/hr, for example, approximately 4009 kg/hr, for example, 4009 kg/hr. In some alternatives, the TEA 99 product stream can include approximately 0.1% by weight of DEA to approximately 0.3% by weight of DEA, for example, 0.1% by weight to 0.3% by weight, for example, approximately 0.17% by weight of DEA, for example, 0.17% by weight of DEA, and TEA 99. Table 1 and Table 2 illustrate these results.

EXAMPLE 2

100% of Base Case Processing Conditions at the TEA Column 125.

The production of ethanolamines as described in Example 1 was further modeled to simulate adding a dummy stream at the TEA column 125. The TEA resultant product stream from the DEA column 122 can be fed to, for example, the eighth stage of the TEA column 125 via line 124. The flow rate for the TEA resultant product stream can be approximately 4100 kg/hr to approximately 4300 kg/hr, for example, 4100 kg/hr to 4300 kg/hr, for example, approximately 4209 kg/hr, for example, 4209 kg/hr. The bottom flow rate of the DEA column 119 via line 121 can be approximately 8300 kg/hr to approximately 8550 kg/hr, for example, 8300 kg/hr to 8550 kg/hr, for example, approximately, 8420 Kg/hr, for example, 8420 kg/hr.

A condenser 206 with a duty of approximately 750 kW to approximately 1100 kW (e.g., 750 kW to 1100 kW), for example, approximately 951 kW (e.g., 951 kW), can keep the top stages of the TEA column 125 at a temperature of approximately 100° C. to approximately 200° C. (e.g., 100° C. to 200° C.), and for example, at approximately 148.1° C. (e.g., 148.1° C.). A reboiler 201, with a duty of approximately 750 kW to approximately 1100 kW (e.g., 750 kW to 1100 kW), and for example, approximately 951 kW (e.g., 951 kW), can keep the bottom stages of the TEA column 125 at a temperature of approximately 150° C. to approximately 200° C. (e.g., 150° C. to 200° C.), and for example, approximately 177.6° C., for example, 177.6° C. TEA column 125 can be operated with a bottom rate of approximately 200 kg/hr to approximately 400 kg/hr (e.g., 200 kg/hr to 400 kg/hr), and for example, approximately 311 kg/hr (e.g., 311 kg/hr). At the TEA column 125, a flow, which can include DEA and TEA can be collected near the head of the TEA column 125 via line 205 and can be condensed in heat exchanger 206. The resulting condensate, which can include negligible quantities of TEA 99, can in part be refluxed into the TEA column 125 via line 207. The remainder of the condensate, which can include TEA 85, approximately 10% by weight of DEA to approximately 15% of DEA (e.g., 10% to 15% by weight of DEA), for example, approximately 15% by weight of DEA (e.g., 15% by weigh of DEA), can be discharged as a dummy stream via line 211, near for example, at the first stage 209 of the TEA column 125. The flow rate of the dummy stream via line 211 can be approximately 400 kg/hr to approximately 800 kg/hr (e.g., 400 kg/hr to 800 kg/hr), for example, approximately 637 kg/hr (e.g., 637 kg/hr).

A TEA 99 product stream recovered from the TEA column 125 can be collected via line 126 near for example, at the fourth stage of the TEA column 125. In some alternatives, the TEA 99 product stream can include approximately 0.01% by weight of DEA to approximately 0.3% by weight of DEA (e.g., 0.01 to 0.3% by weight of DEA), and for example, approximately 0.1% by weight of DEA (e.g., 0.1% by weight of DEA). The TEA 99 product stream can also include approximately 99% by weight of TEA 99 to approximately 100% by weight of TEA 99 (e.g., 99 to 100% by weight of TEA 99), and for example, approximately 99.9% by weight of TEA 99 (e.g., 99.9% by weight of TEA 99). Table 1 and Table 2 illustrate these results.

EXAMPLE 3

110% of Base Case at TEA Column 125

The production of ethanolamines as described in Example 1 was further modeled to simulate increased processing conditions at the TEA column 125. The processing conditions data at the TEA column 125 is adjusted by approximately 5% to approximately 20% over the base case data (e.g., 5% to 20%), and for example, by approximately 10% (e.g., 10%). The processing conditions can include, but are not limited to, condenser heat duty, reboiler heat duty, and bottom flow rate of the TEA column 125. This simulation was labeled as 110% of base case.

The TEA resultant product stream including approximately 10% by weight of DEA to approximately 15% by weight of DEA (e.g.,10% to 15% by weight of DEA), and for example, approximately, 15% by weight of DEA (e.g., 15% by weight of DEA), TEA and byproducts can be fed to, for example, the eighth stage of the TEA column 125 via line 124. The flow rate for the TEA resultant product stream can be approximately 3800 kg/hr to approximately 4200 kg/hr (e.g., 3800 kg/hr to 4200 kg/hr), for example, approximately 4000 kg/hr (e.g., 4000 kg/hr). The bottom flow rate of the DEA column 119 via line 121 can be approximately 9600 kg/hr to approximately 10,000 kg/hr (e.g., 9600 kg/hr to 10,000 kg/hr), for example, approximately, 9802 kg/hr (e.g., 9802 kg/hr). The TEA column 125 can include, for example, eight stages. TEA heavy ends 202 from the bottom of the TEA column 125 can be fed in to, for example, the seventh stage of the TEA column 125 via line 129. A condenser 206 with a duty of approximately 1000 kW to approximately 1600 kW (e.g., 1000 kW to 1600 kW), and for example, approximately 1387 kW (e.g., 1387 kW), can keep the top stages of the TEA column 125 at a temperature of approximately 100° C. to approximately 200° C. (e.g., 100° C. to 200° C.), and for example, at approximately 171.5° C. (e.g., 171.5° C.). A reboiler 201, with a duty of approximately 1000 kW to approximately 1600 kW (e.g., 1000 kW to 1600 kW), and for example, approximately 1371 kW (e.g., 1371 kW), can keep the bottom stages of the TEA column 125 at a temperature of approximately 150° C. to approximately 200° C. (e.g., 150° C. to 200° C., and more preferably, approximately 181.4° C. (e.g., 181.4° C.). TEA column 125 can be operated with a bottom rate of approximately 300 kg/hr to approximately 600 kg/hr (e.g., 300 kg/hr to 600 kg/hr), and for example, approximately 499 kg/hr (e.g., 499 kg/hr).

A stream, which can include trace amounts of TEA 99, TEA heavy ends 202 and byproducts can be collected at the eighth stage 210 of the TEA column 125, and fed to a reboiler 201 via line 203. TEA 99 can be distilled and returned to the TEA column 125 via line 204. The TEA heavy ends 202 stream can exit the heat exchange 201 via line 202 for further processing by the evaporator and TEA column 125. A TEA 99 product stream can be collected, from example, at the fourth stage of the TEA column 125 via line 126. The flow rate of the TEA 99 collected from line 126 can be approximately 3500 kg/hr to approximately 4500 kg/hr (e.g., 3500 kg/hr to 4500 kg/hr), and for example, approximately 3690 kg/hr (e.g., 3690 kg/hr). In some alternatives, the TEA 99 product stream can include approximately 0.1% by weight of DEA to approximately 0.9% by weight of DEA (e.g., 0.1% to 0.9% by weight of DEA), and for example, approximately 0.6% by weight of DEA (e.g., 0.6% by weight of DEA), and TEA 99.

EXAMPLE 4

110% of Base Case at TEA Column 125 with Dummy Stream

The production of ethanolamines as described in Example 3 was further modeled to simulate adding a dummy stream at the TEA column 125. The processing conditions data at the DEA column 122 was reduced by approximately 2% to approximately 4% over the base case data (e.g., 2% to 4%), and for example, by approximately 3% (e.g., 3%). The processing condition includes, but is not limited to, bottom stream flow rate of the DEA Column 122. The TEA resultant product stream from the DEA column 122 can be fed to, for example, the eighth stage of the TEA column 125 via line 124. The flow rate for the product stream can be approximately 4000 kg/hr to approximately 4200 kg/hr (e.g., 4000 kg/hr to 4200 kg/hr), more preferably, approximately 4085 kg/hr (e.g., 4085 kg/hr). The bottom flow rate of the DEA column 119 via line 121 can be approximately 9600 kg/hr to approximately 10,000 kg/hr (e.g., 9600 kg/hr to 10,000 kg/hr), for example, approximately, 9802 kg/hr (e.g., 9802 kg/hr). A condenser 206 with a duty of approximately 750 kW to approximately 1100 kW (e.g., 750 kW to 1100 kW), and for example, approximately 953 kW (e.g., 953 kW), can keep the top stages of the TEA column 125 at a temperature of approximately 100° C. to approximately 200° C. (e.g., 100° C. to 200° C.), and for example, at approximately 148.1° C. (e.g., 148.1° C.). A reboiler 201, with a duty of approximately 750 kW to approximately 1100 kW (e.g., 750 kW to 1100 kW), and for example, approximately 954 kW (e.g., 954 kW), can keep the bottom stages of the TEA column 125 at a temperature of approximately 150° C. to approximately 200° C. (e.g., 150° C. to 200° C.), and for example, approximately 177.5° C. (e.g., 177.5° C.). TEA column 125 can be operated with a bottom rate of approximately 300 kg/hr to approximately 600 kg/hr (e.g., 300 kg/hr to 600 kg/hr), and for example, approximately 499 kg/hr (e.g., 499 kg/hr). At the TEA column 125, a flow, which can include DEA and TEA can be collected near the head of the TEA column 125 via line 205 and can be condensed in heat exchanger 206. The resulting condensate, which can include negligible quantities of TEA 99, can in part be refluxed into the TEA column 125 via line 207. The remainder of the condensate, which can include TEA 85, approximately 10% by weight of DEA to approximately 15% of DEA (e.g., 10% to 15% by weight of DEA), for example, approximately 15% by weight of DEA (e.g., 15% by weight of DEA) can be discharged as a dummy stream via line 211, near for example, at the first plate 209 TEA column 125. The dummy stream can include approximately 500 kg/hr of TEA 85 to approximately 600 kg/hr of TEA 85 (e.g., 500 kg/hr to 600 kg/hr of TEA 85), approximately 90 kg/hr of DEA to approximately 100 kg/hr of DEA (e.g., 90 kg/hr to 100 kg/hr of DEA). For example, the dummy stream can include approximately 550 kg/hr of TEA 85 and approximately 97 kg/hr of DEA (e.g., 550 kg/hr of TEA 85 and 97 kg/hr of DEA). The flow rate of the dummy stream via line 211 can be approximately 400 kg/hr to approximately 800 kg/hr (e.g., 400 kg/hr to 800 kg/hr), for example, approximately 647 kg/hr (e.g., 647 kg/hr). A TEA 99 product stream recovered from the TEA column 125 can be collected via line 126 near for example, at the fourth stage of the TEA column 125. In some alternatives, the TEA 99 product stream can include approximately 0.01% by weight of DEA to approximately 0.3% by weight of DEA (e.g., 0.01% by weight of DEA to 0.3% by weight of DEA), and for example, approximately 0.1% by weight of DEA (e.g., 0.1% by weight of DEA). The TEA 99 product stream can also include approximately 99% by weight of TEA 99 to approximately 100% by weight of TEA (e.g., 99% to 100% by weigh of TEA 99), and for example, approximately 99.9% by weight of TEA 99 (e.g., 99.9% by weight of TEA). Table 1 and Table 2 illustrate these results.

Table 1 shows the output parameters at the TEA column 125. Load is measured in percent (%); top temperature (Top Temp) and bottom temperature (Bottom Temp) are measured in degrees Celsius (° C.), pressure is measured in millibar (mbar), bottom rate and reflux rate are measured in kilograms per hour (kg/hr), and condenser heat duty and reboiler heat duty are measured in kiloWatts (kW).

TABLE 1

Output Parameters at TEA Column 125

| Description | units | PFD % | Simulated without Dummy | Simulated with Dummy TEA 85% | Sim. Actual without Dummy | Sim. Actual with Dummy TEA 85% |
|---|---|---|---|---|---|---|
| Load | % | 100 | 100 | 100 | 110 | 110 |
| Top Temp | ° C. | 171.2 | 171.4 | 148.1 | 171.5 | 148.1 |
| Pressure | mbar | 2.7 | 2.7 | 2.7 | 2.7 | 2.7 |
| Bottom Rate | kg/hr | 325.10 | 311 | 311 | 499 | 499 |
| Bottom Temp | ° C. | 181.2 | 181.4 | 177.6 | 181.4 | 177.5 |
| Pressure | mbar | 4.4 | 4.4 | 4.4 | 4.4 | 4.4 |
| Condenser Heat Duty, Qc | kW | 1789 | 1441 | 951 | 1387 | 953 |
| Reboiler Heat Duty, Qr | kW | 1068 | 1424 | 951 | 1371 | 954 |
| Reflux rate | kg/hr | N/A | 4400 | 4400 | 4400 | 4400 |

Table 2 shows the comparison of the TEA product content for the simulated cases and for the actual plant production rate at the TEA column 125, where load is measured in %, production in kilograms per hour (kg/hr), H20, MEA, DEA, TEA, and MEG are all measured in weight percent (Wt %).

TABLE 2

Comparison of TEA Product Content for Simulations and Actual Plant Production Rate at TEA Column 125

| Description | units | PFD % | Simulated without Dummy | Simulated with Dummy TEA 85% | | Sim. Actual without Dummy | Sim. Actual with Dummy TEA 85% | |
|---|---|---|---|---|---|---|---|---|
| Load | % | 100 | 100 | 100 | | 110 | 110 | |
| Production | kg/h | 99% TEA from product stream | 99% TEA from product stream | 99% TEA from product stream | 85% TEA by Dummy | 99% TEA from product stream | 99% TEA from product stream | 85% TEA by Dummy |
| | | 4000 | 4009 | 3450 | 637 | 3690 | 3128 | 647 |
| H$_2$O | Wt % | 0 | 0 | 0 | 0 | 0 | 0 | 0 |
| MEA | Wt % | 0 | 0 | 0 | 0 | 0 | 0 | 0 |
| DBA | Wt % | 0.17 | 0.6 | 0.1 | 15 | 0.6 | 0.1 | 15 |
| TEA | Wt % | 99.49 | 99.4 | 99.9 | 85 | 99.4 | 99.9 | 85 |
| MEG | Wt % | 0 | 0 | 0 | 0 | 0 | 0 | 0 |

Based on the above results, approximately 5000 tons (e.g., 5000 tons) of TEA 85 per year can be produced via a dummy stream 211 at the TEA column 125 by increasing the bottom stream flow rate of DEA column 122 via line 124 from approximately 20 kg/hr to approximately 200 kg/hr (e.g., 20 kg/hr to 200 kg/hr), and for example, approximately 80 kg/hr (e.g., 80 kg/hr) and reducing the flow rate of the TEA 99 product stream by approximately 10% to approximately 35% (for example, 10% to 35%), and for example, by approximately 15% (e.g., 15%). The increased DEA flow rate and reduced TEA 99 flow rate can result in a decrease in the temperature of the TEA column by approximately 10° C. to approximately 50° C. (e.g., 10° C. to 50° C.), and for example, by approximately 23° C. (e.g., 23° C.). The reduced temperature can result in a triethanolamine product with an APHA color of approximately 0 to less than approximately 50 (e.g., 0 to 50), for example, approximately 0 to approximately 40 (e.g., 0 to 40), for example, approximately 0 to approximately 30 (e.g., 0 to 30), for example, approximately 0 to approximately 20 (e.g., 0 to 20), and for example, approximately 0 to approximately 10 (e.g., 0 to 10). The increased DEA flow rate and reduced TEA 99 flow rate can result in a reduction of the Condenser Heat Duty (Qc) and reboiler heat duty (Qr), by approximately 15% to approximately 50% (e.g., 15% to 50%), and for example, approximately 35% (e.g., 35%).

The systems and methods disclosed herein include at least the following embodiments:

Embodiment 1: A method for producing triethanolamine from a non-reactive distillation column, comprising: mixing an ammonia solution comprising 30% to 40% by weight ammonia with ethylene oxide in a reactor to create a resultant product stream, wherein said resultant product stream comprises ethanolamines, unreacted ammonia and water; removing 30% to 50% by weight of the unreacted ammonia and from the resultant product stream to create a stripped product stream; transferring the stripped product stream to a stage of a diethanolamine distillation column to create a resultant product stream, wherein said resultant product stream comprises triethanolamine with a degree of purity equal to or greater than 85% by weight and 10% to 15% by weight of diethanolamine; adjusting bottom stream flow rate at the diethanolamine distillation column from 1% to 4% above a base value bottom stream flow rate; transferring the resultant product stream to at least one stage of a triethanolamine distillation column to create a triethanolamine product stream, wherein the triethanolamine product stream comprises triethanolamine with a degree of purity greater than or equal to 99% by weight and 0.1% to 0.6% by weight of diethanolamine; adjusting flow rate for the triethanolamine product stream by 10% to 20% below a base value flow rate; and removing a portion of the resultant product stream via a dummy stream to create a triethanolamine resultant stream, wherein said triethanolamine resultant stream comprises triethanolamine with a degree of purity greater than or equal to 85% by weight and 10% to 15% by weight of diethanolamine.

Embodiment 2: The method of Embodiment 1, further comprising receiving TEA heavy ends from an evaporator, wherein said TEA heavy ends comprise triethanolamine and 0.01 kilograms per hour to 0.05 kilograms per hour of diethanolamine, and wherein said TEA heavy ends are transferred to the stage of the triethanolamine column.

Embodiment 3: The method of Embodiment 1 or Embodiment 2, wherein the base value bottom stream flow rate is 3900 kilograms per hour to approximately 4300 kilograms per hour.

Embodiment 4: The method of Embodiment 3, wherein the base value bottom stream flow rate is 4085 kilograms per hour.

Embodiment 5: The method of any of Embodiments 1-4, wherein the base value flow rate is 3000 kilograms per hour to 4000 kilograms per hour.

Embodiment 6: The method of Embodiment 5, wherein the base value flow rate is 3450 kilograms per hour.

Embodiment 7: The method of any of Embodiments 1-6, wherein the adjusted flow rate for the triethanolamine product stream and the adjusted bottom flow rate at the diethanolamine column results in a decrease in temperature at the triethanolamine column by 15° C. to approximately 40° C.

Embodiment 8: The method of Embodiment 7, wherein the decreased temperature is 23.5° C.

Embodiment 9: The method of any of Embodiments 1-8, wherein the triethanolamine distillation column comprises a heat exchanger selected from thermosiphon, a reboiler, or a combination comprising at least one of the foregoing.

Embodiment 10: The method of any of Embodiments 1-9, wherein the ethanolamines are selected from monoethanolamine, diethanolamine, triethanolamine, or a combination comprising at least one of the foregoing.

Embodiment 11: The method of any of Embodiments 1-10, wherein the dummy stream comprises triethanolamine with a degree of purity greater than or equal to 80% and 10% to 15% by weight of diethanolamine.

Embodiment 12: The method of Embodiment 11, wherein the dummy stream comprises triethanolamine with a degree of purity greater than or equal to 85% and 15% by weight of diethanolamine.

Embodiment 13: The method of any of Embodiments 1-12, wherein the flow rate of the dummy stream is 300 kilograms per hour to 800 kilograms per hour.

Embodiment 14: The method of Embodiment 13, wherein the flow rate of the dummy stream is 625 kilograms per hour.

Embodiment 15: The method of any of Embodiments 1-14, wherein the dummy stream exits the triethanolamine distillation column at a temperature of 147° C. to 149° C.

Embodiment 16: The method of Embodiment 15, wherein the dummy stream exits the triethanolamine distillation column at a temperature of 148.1° C.

Embodiment 17: The method of any of Embodiments 1-16, wherein the dummy stream exits the triethanolamine distillation column at a pressure of 2 millibar to 4 millibar.

Embodiment 18: The method of Embodiment 17, wherein the dummy stream exits the triethanolamine distillation column at a pressure of 3 millibar.

Although the foregoing description is directed to the preferred embodiments of the invention, it is noted that other variation and modifications will be apparent to those skilled in the art, and can be made without departing from the spirit or scope of the invention. Moreover, features described in connection with one embodiment of the invention can be used in conjunction with other embodiments, even if not explicitly stated above.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A method for producing triethanolamine from a non-reactive distillation column, comprising:
    mixing an ammonia solution comprising 30% to 40% by weight ammonia with ethylene oxide in a reactor to create a resultant product stream, wherein said resultant product stream comprises ethanolamines, unreacted ammonia and water;
    removing 30% to 50% by weight of the unreacted ammonia and from the resultant product stream to create a stripped product stream;
    transferring the stripped product stream to a stage of a diethanolamine distillation column to create a resultant product stream, wherein said resultant product stream comprises triethanolamine with a degree of purity equal to or greater than 85% by weight and 10% to 15% by weight of diethanolamine;
    adjusting bottom stream flow rate at the diethanolamine distillation column from 1% to 4% above a base value bottom stream flow rate, wherein the base value bottom stream flow rate is 3900 kilograms per hour to approximately 4300 kilograms per hour;
    transferring the resultant product stream to at least one stage of a triethanolamine distillation column to create a triethanolamine product stream, wherein the triethanolamine product stream comprises triethanolamine with a degree of purity greater than or equal to 99% by weight and 0.1% to 0.6% by weight of diethanolamine;
    adjusting flow rate for the triethanolamine product stream by 10% to 20% below a base value flow rate, wherein the base value flow rate is 3000 kilograms per hour to 4000 kilograms per hour; and
    removing a portion of the resultant product stream via a dummy stream to create a triethanolamine resultant stream, wherein said triethanolamine resultant stream comprises triethanolamine with a degree of purity greater than or equal to 85% by weight and 10% to 15% by weight of diethanolamine.

2. The method of claim 1, further comprising receiving TEA heavy ends from an evaporator, wherein said TEA heavy ends comprise triethanolamine and 0.01 kilograms per hour to 0.05 kilograms per hour of diethanolamine, and wherein said TEA heavy ends are transferred to the stage of the triethanolamine column.

3. The method of claim 1, wherein the base value bottom stream flow rate is 4085 kilograms per hour.

4. The method of claim 1, wherein the base value flow rate is 3450 kilograms per hour.

5. The method of claim 1, wherein the adjusted flow rate for the triethanolamine product stream and the adjusted bottom flow rate at the diethanolamine column results in a decrease in temperature at the triethanolamine column by 15° C. to approximately 40° C.

6. The method of claim 5, wherein the decreased temperature is 23.5° C.

7. The method of claim 1, wherein the triethanolamine distillation column comprises a heat exchanger selected from thermosiphon, a reboiler, or a combination comprising at least one of the foregoing.

8. The method of claim 1, wherein the ethanolamines are selected from monoethanolamine, diethanolamine, triethanolamine, or a combination comprising at least one of the foregoing.

9. The method of claim 1, wherein the dummy stream comprises triethanolamine with a degree of purity greater than or equal to 80% and 10% to 15% by weight of diethanolamine.

10. The method of claim 9, wherein the dummy stream comprises triethanolamine with a degree of purity greater than or equal to 85% and 15% by weight of diethanolamine.

11. The method of claim 1, wherein the flow rate of the dummy stream is 300 kilograms per hour to 800 kilograms per hour.

12. The method of claim 11, wherein the flow rate of the dummy stream is 625 kilograms per hour.

13. The method of claim 1, wherein the dummy stream exits the triethanolamine distillation column at a temperature of 147° C. to 149° C.

14. The method of claim 13, wherein the dummy stream exits the triethanolamine distillation column at a temperature of 148.1° C.

15. The method of claim 1, wherein the dummy stream exits the triethanolamine distillation column at a pressure of 2 millibar to 4 millibar.

16. The method of claim 15, wherein the dummy stream exits the triethanolamine distillation column at a pressure of 3 millibar.

17. The method of claim 1, wherein the resultant triethanolamine resultant stream has an APHA color of 0 to 50.

* * * * *